United States Patent [19]

Kulle

[11] 4,346,704
[45] Aug. 31, 1982

[54] SLEEVE VALVE FOR PARENTERAL SOLUTION DEVICE

[75] Inventor: Lee K. Kulle, Mundelein, Ill.

[73] Assignee: Baxter Travenol Laboratories, Inc., Deerfield, Ill.

[21] Appl. No.: 185,478

[22] Filed: Sep. 9, 1980

[51] Int. Cl.³ .............................................. A61M 5/14
[52] U.S. Cl. ............................ 128/214 R; 137/516.15; 137/860
[58] Field of Search ............ 128/214 R, 214 B, 214.2, 128/274, 227; 137/516.15, 853, 860

[56] References Cited

U.S. PATENT DOCUMENTS

| | | | |
|---|---|---|---|
| 2,538,662 | 1/1951 | Abbott | 128/274 X |
| 2,551,315 | 5/1951 | Christopher et al. | 128/227 |
| 2,743,724 | 5/1956 | Gispen | 128/216 |
| 3,459,217 | 8/1969 | Callahan | 128/860 X |
| 3,601,151 | 8/1971 | Winnard | 137/860 |
| 3,794,043 | 2/1974 | McGinnis | 137/853 X |
| 4,063,555 | 12/1977 | Ulinder | 128/274 X |
| 4,290,454 | 9/1981 | Shetler | 137/853 |

FOREIGN PATENT DOCUMENTS 733890  7/1955  United Kingdom ................ 137/860

Primary Examiner—Dalton L. Truluck
Attorney, Agent, or Firm—John P. Kirby, Jr.; Bradford R. L. Price; George H. Gerstman

[57] ABSTRACT

A sleeve valve is carried in a parenteral solution administration device. The valve comprises an outer housing (30) defining an outlet tube (28); an inner tubular support (38) defining an inlet tube (45) and a closed forward end positioned within the outlet tube. Lateral aperture means (46) are provided in the tubular support, and an elastic tube (40) surrounds the inner tubular support to cover the lateral apertures. The inner tubular support is free of elastic, tube-retaining structures at its closed end, and is adapted to permit the elastic tube to be laterally slidable on the inner, tubular support through a limited distance. The outer housing defines vanes (44) to limit the lateral advancement of the elastic tube on the support, while shoulder means (42) are positioned about the support to limit the lateral retraction of the elastic tube away from the closed end. Accordingly, pressurized fluid flow though the inlet tube causes expansion of the elastic tube by pressure to permit fluid flow between the tube and tubular support out of both ends of the elastic tube. The valve can have higher flow rates at lower pressures, while at the same time having a lower residual volume.

12 Claims, 3 Drawing Figures

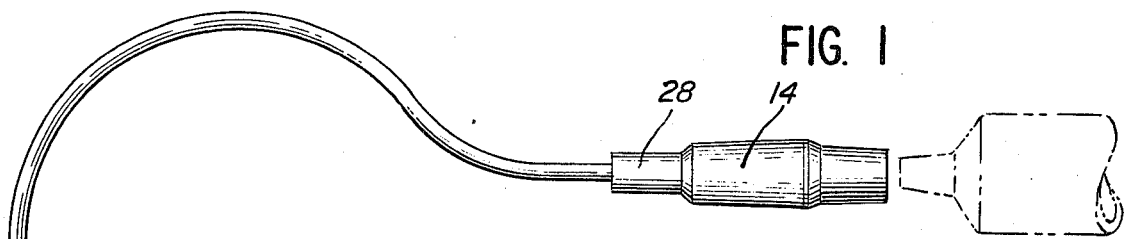
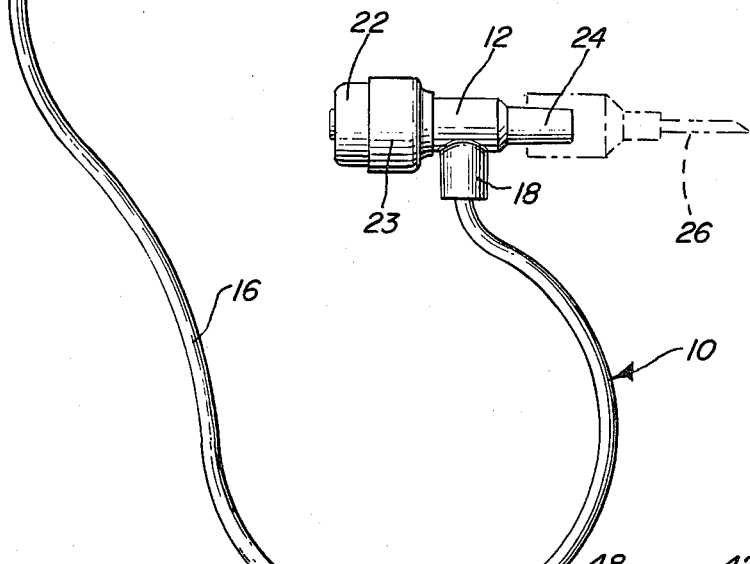
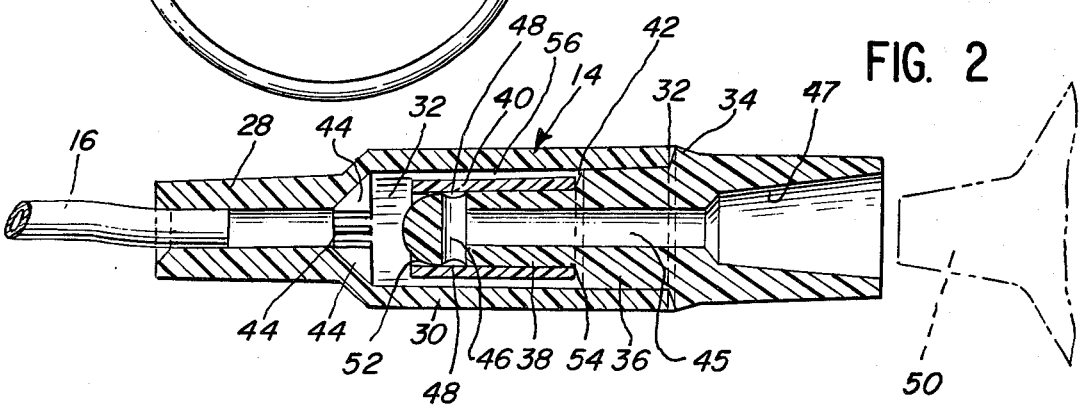
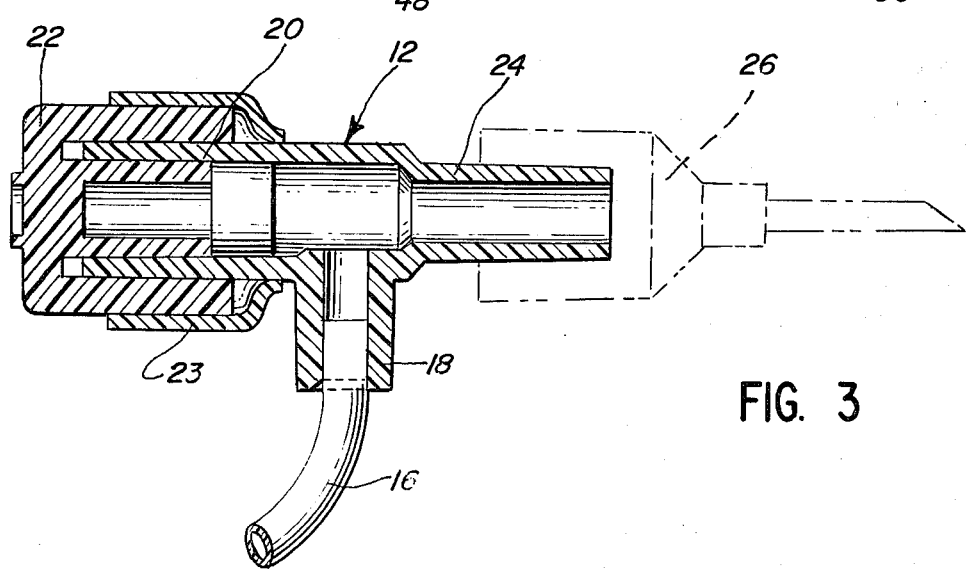

SLEEVE VALVE FOR PARENTERAL SOLUTION DEVICE

INDUSTRIAL APPLICABILITY

This application relates to an improved one-way valve of the sleeve valve type. The valve may particularly be used in medical sets and especially sets for the intravenous administration of anesthetic.

BACKGROUND ART

Anesthetic administration sets for intravenous administration are commercially available. A typical set may include two components separated by a substantial length of tubing, for example about 30 inches in length. The forward component of the set may include a T-shaped luer connector structure with a needle adapter at one branch of the T, an injection site at the other branch of the T (to permit connection by the main IV set), and with the base of the T communicating with the 30 inch tubing.

At the other end of the 30 inch tubing, a housing containing a one-way valve is provided, plus a luer for receiving a syringe for anesthetic or other medication to be provided in critical quantities. Accordingly, during an operation, the anesthesiologist can stand behind the surgeon or otherwise out of the way, and yet can administer anesthetic to the patient by forcing the parenteral anesthetic through the one-way valve by means of pressure on the syringe, with the anesthetic passing through the tube to the T-connector, and from there into the patient's bloodstream. The one-way valve prevents backflow due to any hydrostatic pressure head of a connected IV set carrying parenteral solution, or due to the venous pressure of the patient.

One commercially available set of the above type includes a one-way sleeve valve in which the rubber sleeve has a closed end about the inlet orifice so that liquid must pass about the inner surface of the closed end, and then move rearwardly about the orifice until the inner end of the sleeve is passed. Then it turns 180° and flows along the outer surface of the sleeve outwardly on its path to the patient. Such a design is of the general type as shown in Winnard U.S. Pat. No. 3,601,151.

This commercially available design, however, exhibits an excessively high resistance to flow. Also the residual volume of the set is unduly high, so that the surgeon is forced to inject an excess amount of anesthetic, for example, above and beyond that calculated for the patient's need, since an unduly high amount of anesthetic remains caught in the inner volume of the set, and is not provided to the patient.

Furthermore, the closed-end sleeve structure can shift, and can block the outlet orifice if it does shift, rendering the valve possibly inoperative.

Numerous other designs of sleeve valves are also known, but each of them are seen to exhibit certain disadvantages relative to the valve of this invention. For example, the sleeve valve shown in Pennisi U.S. Pat. No. 3,384,113 utilizes a seal ring at the rear of the flexible valve sleeve, to prevent its sliding on the inner tubular support.

This results in a more complex structure, requiring a higher pressure for operation, all other things being equal, since flow out of the rear of the flexible sleeve is completely eliminated.

In Gispen U.S. Pat. No. 2,743,724, a tubular sleeve rests upon a tubular support in an annular recess on the tubular support. Thus, the contact surface between the inner surface of the flexible sleeve and the outer surface of the tubular support is recessed, resulting in a higher pressure resistance, all other things being equal upon operation. Also, upon heavy flow pressures, the flexible sleeve can be blown out of its annular recess, changing the operation of the valve.

Finally, in British Pat. No. 733,890, a tubular sleeve is provided on a tubular inner support in which the free end of the inner support is flared outwardly to serve as a retainer for the tubular sleeve. This also increases the flow resistance of the valve flow, requiring higher pressures since the outer, flared end of the inner support serves as an added flow resistance.

The present invention provides a sleeve valve for a parenteral solution administration set or the like having low residual volume, so that critical medications may be administered in precise quantities and with less waste, while at the same time, the valve provides higher flow rates at lower pressures, in comparison with the structures of the prior art.

DISCLOSURE OF THE INVENTION

In accordance with this invention, a sleeve valve is carried in a parenteral solution administration device. The valve comprises an outer housing defining an outlet tube and an inner tubular support defining an inlet tube, and having a closed, forward end positioned within the outer housing. Lateral aperture means communicate between the bore of the tubular support and the exterior thereof through the tubular support. An elastic tube is provided, surrounding the inner tubular support to cover the lateral aperture means.

In accordance with this invention, the inner tubular support is free of elastic tube-retaining structures such as is found in the prior art at its closed end, the tubular support being also adapted to permit the elastic tube to be laterally slidable on the inner tubular support through a limited distance.

The outer housing defines vane means to limit the lateral advancement of the elastic tube on the support, while shoulder means are positioned about the support to limit the lateral retraction of the elastic tube away from the closed end.

The elastic tube covers the apertures in all of its lateral sliding positions. As the result of this, upon pressurized fluid flow through the inlet tube, the elastic tube is expanded by pressurized fluid passing through the lateral aperture means, to permit fluid flow between the tube and tubular support out of both ends of the elastic tube. The resulting fluid flow proceeds through the valve means and then through the outlet tube.

By means of this construction, one-way sleeve valve having a low back pressure is provided in which the sleeve is not rigidly retained in any way, but freely floats during flow conditions on the tubular support. Despite this, the front end of the tube is open and without significant flow constricting means retaining it on the support. Instead a few (typically three or four) thin vanes are positioned to cross the plane of the junction between the outer end of the elastic tube and the inner tubular support in minimally flow restricting manner so that an open, laminar, unrestricted flow is provided out of the sleeve valve. At the same time, additional flow capacity is provided by the fact that the rear of the elastic tube is also free to open and to contribute additional flow communication to the area outside of the elastic tube.

The vanes permit unencumbered flow of fluid between them, with the vanes being preferably positioned radially about one end of the axis of the elastic tube.

Preferably the elastic tube is spaced from the inner wall of the outer housing to permit fluid flow along both the inner and outer surfaces of the elastic tube.

To reduce the residual volume of the sleeve valve of this invention, as is desirable, the inner diameter of the outer housing is preferably not more than 0.25 inch. The inner diameter of flexible tubing connecting the sleeve valve of this invention may also preferably be no more than about 0.05 inch for minimizing the residual volume.

Thus the residual volume of the valve of this invention may be no more than 0.190 ml., for example: 0.182 ml., but typically at least 0.17 ml.

BRIEF DESCRIPTION OF THE DRAWINGS

In the drawings,

FIG. 1 is a plan view of a typical anesthetic administration set utilizing the invention of this application.

FIG. 2 is an enlarged longitudinal sectional view of the sleeve valve of this invention as utilized in the anesthetic administration set of FIG. 1.

FIG. 3 is an enlarged longitudinal sectional view of the T-shaped luer connector structure utilized in the anesthetic administration set of FIG. 1.

BEST MODE FOR CARRYING OUT THE INVENTION

Referring to the drawings, anesthetic administration set 10 is provided with a T-connector 12 at one end and a one-way valve assembly 14 at the other, being connected by about 30 inches of flexible tubing 16 which may be conventionally made of polyvinyl chloride plastic, typically having an inner diameter of 0.049 inch.

T-connector 12 may be of conventional design, as described above, with the base 18 of the T-connector being a reception port for tubing 16. Arm 20 of the T-connector 12 may carry a conventional latex injection site 22, retained by a shrink band 23, while arm 24 may serve as a luer for an intravenous needle 26 or the like, or may serve as a connection to another solution administration set, as may be desired.

One-way valve housing 14 carries port 28 which may be sealed to the other end of tubing 16. Port 28 is shown to be an integral part of outer housing 30, which may be molded out of a rigid plastic, for example ABS plastic, and may contain a tubular housing chamber 32 having an inner diameter of about 0.19 inch, for example.

Outer housing 30 may be sealed, for example by sonic welding at a joint defined at end 32 to an annular flange 34 carried by an inner tubular support housing 36, which may be integrally molded also out of a rigid plastic such as ABS plastic, and which carries the inner tubular support 38 previously discussed. An elastic tube 40, which may be made of silicone rubber or any other desired elastomer material, is positioned on tubular support 38.

Annular shoulder 42 is defined at the rear end of tubular support 38, and serves to limit the lateral retraction of elastic tube 40.

Radially positioned vanes 44 (specifically shown to be spaced 90° apart) are carried by outer housing within chamber 32 to limit the forward lateral advance of sleeve 40, preventing its removal from inner tubular support 38. They may be positioned radially about one end of the axis of elastic tube 40.

Inner support housing 36 also defines a conduit 45 which terminates at its inner end in a pair of branch conduits 46 and apertures 48, so that pressurized fluid from conduit 44 can pass into the space between elastic tube 40 and inner tubular support 38. The rear end 47 of conduit 45 is flared in the appropriate manner of a luer connection to receive the tapered end 50 of a syringe as shown, which syringe may contain the liquid medicament such as anesthetic.

Accordingly, when the syringe is in place and anesthetic or other medicament is forced into conduit 45, the pressurized fluid expands the space between inner tubular support 38 and elastic tube 40, allowing flow out of the front end 52 of the annular space thus formed.

Typically, liquid flow also passes out of the annular end 54 of the space between inner tubular support 38 and elastic tube 40, to permit additional liquid flow from this annular end outwardly to the space 56 between outer housing 30 and elastic tube 40, to provide additional flow paths and a reduced back pressure for the valve. The resulting flow from both ends 52 and 54 combines in the vicinity of vanes 44, and flows through port 28 into tube 16, to be conveyed to T-connector 12, and from there to the patient through needle 26, with a minimum of residual volume wastefully retaining medicament and with a low back pressure. The elastic tube 40 can "float" during operation on inner support housing 38 for improved operation.

Also it can be seen that the improved structure of this invention is a very simple, reliable and low cost design for production of disposable units.

The above has been offered for illustrative purposes only, and is not intended to limit the invention of this application, which is as defined in the claims below.

That which is claimed is:

1. In a sleeve valve carried in a parenteral solution administration device, which valve comprises an outer housing defining an outlet tube; an inner tubular support defining an inlet tube and having a closed forward end positioned within the outer housing, plus lateral aperture means communicating between the bore of said tubular support and the exterior thereof; and an elastic tube surrounding said inner tubular support to cover said lateral aperture means, the improvement comprising, in combination:

said inner tubular support being free of elastic, tube-retaining structure means at its closed end and adapted to permit said elastic tube to be laterally slidable on said inner tubular support through a limited distance, said outer housing defining vane means to limit the lateral advancement of said elastic tube on said support, and shoulder means positioned about said support to limit the lateral retraction of said elastic tube away from the closed end, said elastic tube covering said apertures in all lateral sliding positions, whereby, upon pressurized fluid flow through said inlet tube, said elastic tube is expanded by pressure to permit fluid flow between said tube and tubular support out of both ends of the elastic tube, the resulting flow proceeding through said vanes and said outlet tube.

2. The sleeve valve of claim 1 in which said elastic tube is spaced from the inner wall of said outer housing.

3. The sleeve valve of claim 2 in which said outer housing and inner tubular support are made of ABS plastic.

4. The sleeve valve of claim 2 in which said elastic tube is made of silicone rubber.

5. The sleeve valve of claim 2 in which the inner diameter of said outer housing is no more than 0.25 inch to provide a minimal residual volume of fluid inside.

6. The sleeve valve of claim 2 in which said outer housing and inner tubular support are connected at a joint defined by an end of said outer housing and an annular projection about the exterior of said inner tubular support.

7. The sleeve valve of claim 2 in which said vanes are positioned radially about one end of the axis of the elastic tube.

8. In a sleeve valve carried in a parenteral solution administration device including a luer adapter for receiving intravenous needle and an injection site for aseptic communication with the interior of said set, connected by flexible tubing to a sleeve valve assembly, said sleeve valve assembly carrying luer adapter means for connection with a syringe, said sleeve valve assembly also containing said sleeve valve which comprises, an outer housing defining an outlet tube; an inner tubular support defining an inlet tube having a closed, forward end positioned within the outer housing, plus lateral aperture means communicating between the bore of said tubular support and the exterior thereof; and an elastic tube surrounding said inner tubular support to cover said lateral aperture means, the improvement comprising, in combination: said inner tubular support being free of elastic, tube-retaining structure means at its closed end and adapted to permit said elastic tube to be laterally slidable on said inner tubular support through a limited distance, said outer housing defining vane means to limit the lateral advancement of said elastic tube on said support, and shoulder means positioned about said support to limit the lateral retraction of said elastic tube away from the closed end, said elastic tube covering said apertures in all lateral sliding positions, whereby, upon pressurized fluid flow through said inlet tube, said elastic tube is expanded by pressure to permit fluid flow between said tube and tubular support out of both ends of the elastic tube, the resulting flow proceeding through said vanes and said outlet tube.

9. The sleeve valve of claim 8 in which the inner diameter of said outer housing is no more than 0.25 inch to provide a minimal residual volume of fluid inside.

10. The sleeve valve of claim 9 in which said elastic tube is spaced from the inner wall of said outer housing.

11. The sleeve valve of claim 10 in which said outer housing and inner tubular support are connected at a joint defined by an end of said outer housing and an annular projection about the exterior of said inner tubular support.

12. The sleeve valve of claim 11 in which said vanes are positioned radially about one end of the axis of the elastic tube.

* * * * *